United States Patent [19]

Kosswig et al.

[11] 4,303,544
[45] * Dec. 1, 1981

[54] ADDUCTS OF ALCOHOLS AND OLEFIN OXIDES AS BIODEGRADABLE AND LOW-FOAMING TENSIDES USEFUL IN DETERGENTS

[75] Inventors: Kurt Kosswig; Ekkehard Wienhoefer, both of Marl, Fed. Rep. of Germany

[73] Assignee: Chemische Werke Huels, A.G., Marl, Fed. Rep. of Germany

[*] Notice: The portion of the term of this patent subsequent to Nov. 24, 1998, has been disclaimed.

[21] Appl. No.: 146,918

[22] Filed: May 5, 1980

[30] Foreign Application Priority Data

May 4, 1979 [DE] Fed. Rep. of Germany ....... 2918047

[51] Int. Cl.³ ...................... C07C 41/02; C07C 43/10; C11D 1/722; C11D 3/075
[52] U.S. Cl. .................................. 252/174.21; 252/99; 252/135; 252/358; 568/624; 568/625
[58] Field of Search .............................. 568/624, 625; 252/174.21, 99, 135, 358

[56] References Cited

U.S. PATENT DOCUMENTS

| | | | |
|---|---|---|---|
| 3,340,309 | 9/1967 | Weipert | 568/625 |
| 3,380,925 | 4/1968 | Blaser et al. | 252/174.21 X |
| 3,475,499 | 10/1969 | Winnick | 568/623 X |
| 3,637,869 | 1/1972 | Seizinger | 252/174.21 X |
| 3,706,714 | 12/1972 | Lloyd et al. | 528/76 |
| 3,748,276 | 7/1973 | Schmolka | 252/316 |
| 3,829,505 | 8/1974 | Herold | 568/618 X |
| 3,829,506 | 8/1974 | Schmolka et al. | 568/624 |
| 4,094,797 | 6/1978 | Newkirk et al. | 252/8.9 |

OTHER PUBLICATIONS

Schoenfeldt, *Surface Active Ethylene Oxide Adducts*, Pergamon Press, Oxford, 1969, pp. 659 et seq.

*Primary Examiner*—Dennis L. Albrecht
*Attorney, Agent, or Firm*—Millen & White

[57] ABSTRACT

A compound of the formula

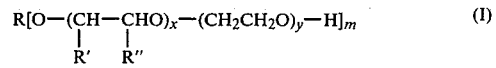

(I)

or

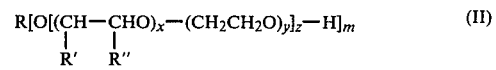

(II)

wherein
R is alkyl of 8–22 carbon atoms in the alkyl chain or hydroxyalkyl of 2–22 carbon atoms; and R' and R" each independently is hydrogen or $C_1$–$C_{20}$-alkyl provided that R' and R" are not simultaneously hydrogen, and R' and R" in total have 8–20 carbon atoms;

and
in I, x is 0.5–5 and y is 5–50; and
in II, z is freely selectable with the proviso that the sum total of all x for a given z is 0.5–5 and the sum total of all y for a given z is 5–50;
and m is 1 or 2.

18 Claims, No Drawings

ADDUCTS OF ALCOHOLS AND OLEFIN OXIDES AS BIODEGRADABLE AND LOW-FOAMING TENSIDES USEFUL IN DETERGENTS

CROSS REFERENCE TO RELATED APPLICATIONS

This application is related to copending application Ser. No. 146,988, filed on even date.

BACKGROUND OF THE INVENTION

Low-foaming tensides having good surfactant and cleansing properties are required in household dishwashers, and also have a corresponding use in commercial fields. Thus, solid, pulverized detergents for dishwashers, for example, frequently contain 1-3% by weight of such tensides in addition to the customary ingredients such as pentasodium triphosphate, sodium silicate, sodium carbonate, sodium aluminate, compounds splitting off chlorine and scenting agents. Liquid compositions used for mechanical cleansing and as additives for clear and sparkling clean rinsing can even contain 15-25% by weight of such tensides.

Tensides satisfying the above prerequisites include, for example, propylene oxide-ethylene oxide polymers known under the trade name of "PLURONICS" (U.S. Pat. No. 2,674,619). In these compounds, the molecular units based on propylene oxide have a lipophilic character whereas the segments formed by ethylene oxide are considered hydrophilic.

The tensides structured in this way, however, have the grave disadvantage that they are biodegradable only with great difficulty. In this age where environmental protection has gained increasing significance in all areas, this property, of course, extensively restricts their useability. For example, a biodegradability of at least 80% is required in the Federal Republic of Germany under the "Antipollution Act Regarding Detergents and Cleansing Agents" of Aug. 20, 1975 ("Detergent Law") and the concomitantly issued "Regulation Regarding the Degradability of Anionic and Nonionic Surfactants in Detergents and Cleansing Agents" of Jan. 30, 1977. The criterion is the so-called "OECD Confirmatory Test" by means of which the residual content of a sample solution of nonionic surfactants is determined using the bismuth activity measurement according to Wickbold. Although ethylene oxide-propylene oxide block and copolymers do not meet this requirement, their use was still permitted for another three years during which a replacement was to be found.

In addition to these polymers, containing only ethylene oxide and propylene oxide or perhaps diamines, another class of compounds is utilized for low-foaming tensides in the above-mentioned areas. These can be considered as unilaterally blocked oligomers of ethylene oxide-propylene oxide units (DOS [German Unexamined Laid-Open Application] No. 1,593,043). These compounds are obtained by addition of alkylene oxides to suitable starting compounds having active hydrogen atoms, such as fatty alcohols or alkyl phenols. The character of the resultant tenside can be varied within limits by suitable choice of block or mixed addition. The advantage of these surface-active compounds resides in the fact that they are more susceptible to biological attack than the "PLURONIC" types. Although they fulfill the requirements of the OECD Confirmatory Test, they are still in need of improvement, as was found by testing their degree of complete remineralization.

If it is desired to avoid the danger factor caused by the formation of metabolites which, in turn, resist further degradation or are even toxic, the use of maximally extensively remineralizable compounds must be preferred. Remineralization means that, for example, a compound made up of carbon, hydrogen, and oxygen, as represented by most of the nonionic tensides, for example, is converted into carbon dioxide and water. The requirement for a satisfactory remineralization is met if values of 50% and above are reached in the biodegradation test measuring the degree of complete remineralization. However, this condition is attained only by an extremely gradual reaction of propylene oxide adducts and even more so by butylene oxide adducts, as was demonstrated by investigations of Fischer (VI. Int. Kongr. grenzfl. akt. Stoffe [Sixth International Congress for Surfactants] Zurich, 1972, 3:745 et seq., especially page 747).

The derivatives of such epoxides heretofore used as low-foaming tensides thus do not provide a satisfactory solution to the problem from an ecological viewpoint.

SUMMARY OF THE INVENTION

It is, accordingly, an object of this invention to provide a solution to the aforementioned problems by providing low-foaming tensides useful for commercial and household dishwashers, having a satisfactory biodegradability calculated as the degree of complete remineralization.

Upon further study of the specification and appended claims, further objects and advantages of this invention will become apparent to those skilled in the art.

These objects have been achieved by this invention by providing a compound of the Formulae I and/or II

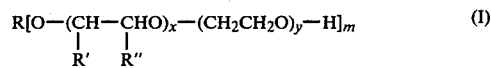

or

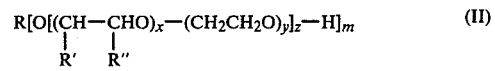

wherein
R is alkyl of 8-22 carbon atoms in the alkyl chain or hydroxyalkyl of 2-22 carbon atoms; and R' and R" each independently is hydrogen or $C_1$-$C_{20}$-alkyl provided that R' and R" are not simultaneously hydrogen, and R' and R" in total have 8-20 carbon atoms;
and
  in I, x is 0.5-5 and y is 5-50; and
  in II, z is freely selectable with the proviso that the sum total of all x for a given z is 0.5-5 and the sum total of all y for a given z is 5-50;
  and m is 1 or 2.

In this connection, it is especially surprising that a substantial enlargement of the alkyl residue in the added 1,2-epoxyalkane portion achieves from a high to a very high remineralizability of the resultant novel tensides, despite the fact disclosed by the above-cited Fischer reference that butylene oxide adducts show a lower degradability than propylene oxide adducts. Therefore, considerable inventive ingenuity had to be expended in order to overcome the existing prejudice in order to develop the present invention.

That is, this invention provides a biodegradable and low-foaming tenside of the formula (I) or (II)

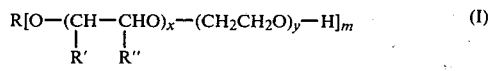 (I)

or

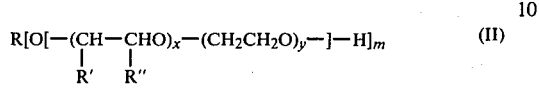 (II)

wherein

R is $C_{8-22}$ alkyl or $C_{2-22}$ hydroxyalkyl; and R' and R" each independently is hydrogen or $C_1$–$C_{20}$-alkyl provided that R' and R" are not simultaneously hydrogen, and R' and R" in total have 8–20 carbon atoms;

x is 0.5–5 and y is 5–50;

"- - -" indicates that the individual x units and the individual y units may be attached to the other x and y units in any order; and m is 1 or 2.

DETAILED DISCUSSION

The compounds of this invention can be prepared, e.g., by adding a conventional acidic or alkaline alkoxylation catalyst to a compound $R(OH)_{1-2}$ having active hydrogen; and reacting this reaction mixture at a suitable temperature with an epoxide

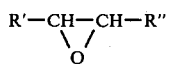

and ethylene oxide.

Alkyl moieties in R in Formulae I and II include those in starting compounds $R(OH)_{1-2}$ suitable for use in the mentioned process of this invention, including, for example, straight-chain and branched, optionally substituted, primary and secondary alcohols of 8–22 carbon atoms, such as 1-octanol, 2-octanol, 1-decanol, 1-undecanol, 2-undecanol, 1-dodecanol, 1-tridecanol, 2-tridecanol, 1-tetradecanol, 1-hexadecanol, 1-octadecanol, 1-eicosanol, 1-docosanol, 2-ethylhexanol, etc.; mixture of alcohols of native origin, i.e. alcohols from vegetable or animals fats, prepared by hydrogenation; alcohols prepared in the Ziegler synthesis and subsequent oxidation, or mixtures thereof (N. Schoenfeldt, Surface Active Ethylen Oxide Adducts, Pergamon Press 1969, page 81), whose disclosure is incorporated by reference herein, as well as the products of hydroformylation or hydrocarboxymethylation of terminally positioned and internally positioned olefins and subsequent hydrogenation (Schoenfeldt, Surface Active Ethylen Oxide Adducts, Pergamon Press 1969, page 82), whose disclosure is incorporated by reference herein; 1,2-, 1,3- and α,ω-alkane-diols of 2–22 carbon atoms, such as ethylene glycol, propylene glycol, 1,3-propanediol, 1,3-butanediol, 1,4-butanediol, 1,2-hexanediol, 1,2-octanediol, 1,2-decanediol, 1,2-dodecanediol, 1,2-tetradecanediol, 1,2-hexadecanediol, 1,2-octadecanediol, 1,2-eicosanediol, 1,2-docosanediol, etc. $R(OH)_{1-2}$ is preferably $C_{8-22}$ fatty alcohols or mixtures thereof or $C_{8-22}$-1,2-alkanediols.

When R is alkyl, it preferably is of 10–20 carbon atoms and when R is hydroxyalkyl, it is preferably of 10–20 carbon atoms. Most preferably, R is alkyl and contains 12–18 carbon atoms. If R is hydroxyalkyl, m is 1.

In the formulae (I and/or II) it is possible for the two epoxy-based units (m-units) to be different from one another, although usually they are identical.

Suitable R' and R" moieties of formulae I and II include those in the starting epoxide components of the formula

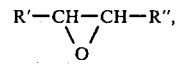

e.g., 1,2-epoxides of 10–22 carbon atoms, central-positioned epoxides of the same carbon number, as well as mixtures thereof.

Especially suitable are epoxides of 14–22 carbon atoms.

Thus, it is possible to use, for example, 1,2-epoxydecane, 1,2-epoxydodecane, 1,2-epoxytetradecane, 1,2-epoxyhexadecane, 1,2-epoxydodecane/tetradecane/hexadecane as a mixture, 1,2-epoxyoctadecane, 1,2-epoxyeicosane, 5,6-epoxydodecane, 7,8-epoxyhexadecane, 7,8-epoxyoctadecane, As well as the product of the reaction of a mixture of central-positioned olefins of 11–15 carbon atoms with a suitable percarboxylic acid, etc. Preferred are 1,2-epoxyalkanes of 12–16 carbon atoms or mixtures thereof.

Preferred values of x and y are as follows: for Formula I, x is 2–3 and y is 20–30; and for Formula II, the sum of all x (z) is 2–3 and the sum of all y (z) is 20–30. Preferred values of x, y and z are, of course, to be selected in accordance with the preferred component weight percentages mentioned below which, in turn, are determined in accordance with the requirements on hydrophilic/lipophilic characteristics.

Thus, in the process of this invention, the relative amounts of reactant materials are determined in accordance with the desired final values of x, y and z assuming complete reaction.

In Formula I the block polymer may be prepared using techniques which are fully conventional, e.g. see U.S. Pat. No. 2,828,345, e.g. see examples 1 and 2 herein.

A particularly desired order of the structural units x, y and z can be achieved by adding alternately the epoxide and ethylene oxide in the desired amounts.

The quantitative ratios of hydroxyhydrocarbon, epoxide, and ethylene oxide with respect to one another should be such that 20–80% by weight, preferably 30–70% by weight, and especially preferably 40–60% by weight of the molecule is lipophilic, while the remainder is hydrophilic. The parts of the molecule derived from the hydroxyhydrocarbon starting compound and from the epoxide

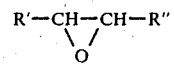

are lipophilic; in contrast, the segments derived from the ethylene oxide are derived from the ethylene oxide are hydrophilic. For example, a tenside composed of one mole of 1-dodecanol, 3 moles of 1,2-epoxytetradecane, and 30 moles of ethylene oxide, accordingly, has a corresponding lipophilic:hydrophilic ratio of 38%:62% and, thus, is within the preferred range. In general, the HLB value of the tensides of this invention is in the range of 4–16, preferably 6–14, most preferably 8–12.

When using a preferred $C_8$-$C_{22}$ fatty alkyl primary alcohol as the starting compound and 1,2-epoxyalkanes of 10–22 carbon atoms, and achieving the preferred ratio between the lipophilic and hydrophilic proportions in the desired final product, the molecular weights of the thus-produced tensides are generally 800–2,500. If other special alcohols or epoxides are required or desired for special purposes, the molecular weights can, of course, lie markedly outside of this range.

Suitable catalysts for the addition reaction of the epoxides

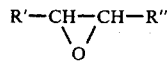

and ethylene oxide to the alcohols are preferably alkaline compounds, such as potassium hydroxide, sodium hydroxide, or the corresponding alcoholates of 1–4 carbon atoms, such as sodium methylate, sodium ethylate, potassium tert-butanolate, etc. However, it is also possible to utilize acidic catalysts, such as boron trifluoride or complex oxonium or carbenium salts, e.g., triethyloxonium tetrafluoroborate. Generally, 0.1–3 wt.% based on the total weight of $R(OH)_{1-2}$ is used (see N. Schoenfeldt, Surface Active Ethylene Oxide Adducts, Pergamon Press 1969, page 102, where the conventional catalysts are discussed.

The addition of the alkylene oxide components to the starting material $R(OH)_{1-2}$ can be controlled so that either block or mixed adducts are produced. The primary reaction of the starting alcohol to produce the block adduct, having, e.g., a 1,2-epoxyalkane block followed by subsequent ethylene oxide addition requires, in the first stage, a temperature of 210°–230° C., whereas temperatures of only 150°–170° C. are necessary in the second stage to conduct the desired reaction within a satisfactory time period. The first stage is generally conducted for 1–2 hours, and the second stage for 1–2 hours.

However, for the simultaneous reaction of the starting alcohol with epoxide and ethylene oxide to produce the mixed adduct, a temperature of 180°–200° C. is sufficient, since the reaction of the epoxide

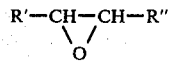

is enhanced by the presence of the very reactive ethylene oxide. Reaction times are generally 2–3 hours.

The foregoing reaction details are appropriate for basic catalysts. When acidic catalysts are utilized, the reaction temperatures are generally lower, e.g., in the first stage, 100°–130° C. for 1–2 hours, and in the second stage, 80°–90° C. for 1–2 hours; and for the preparation of the mixed adduct, 90°–120° C. for 2–3 hours.

These reactions can be carried out under normal pressure, but advantageously a superatmospheric pressure of 1.5–4 atmospheres can be employed.

The techniques for achieving any order of the various x and y units in the tensides of this invention, e.g., various block structures are fully conventional, as are the reaction conditions and operations not described in detail herein. See, for example, U.S. Pat. No. 2,828,345, whose disclosure is incorporated by reference herein. In general, the reaction is completed to an extent of 95–100%.

The block adducts have proved to have a somewhat better water solubility. The capability of lowering the surface tension of water is, however, the same for both groups of compounds and reaches values of 30–35 mN/m for 2% strength solutions in fully demineralized water, as is also found for various known tensides.

The novel tensides of this invention, however, are especially advantageous in their response to the biodegradability test. They pass the OECD Confirmatory Test very satisfactorily with a rate of >90% decline of bismuth-active substance, just as do all surfactants having an n-alkyl chain with a c-number approximately in the fatty alkyl range. In addition, they also exhibit a surprisingly high degree of remineralizability. As measured by the so-called "coupled units" test based on the effluent from a model sewage treatment plant using the "dissolved organic carbon" (DOC) method [W. Janicke, Water Research 5, 917 (1971)]. values of 50–80% are obtained, the higher values being registered by the block adducts, the lower by the mixed adducts. The findings available in the literature (W. K. Fischer, see above) regarding the remineralizability of adducts of propylene and butylene oxide with fatty alcohols and fatty alcohol oxyethylates, are in clear contradiction to these data. As compared with propylene oxide derivatives, the preferred state of the art low-foaming tensides, the products of this invention must thus be considered clearly superior from an ecological viewpoint.

The tensides of this invention are thus suitable as the tenside component in detergent compositions along with other customary additives such as those mentioned above. (See also N. Schoenfeldt, Surface Active Ethylen Oxide Adducts, Pergamon Press 1969, page 424–441 whose disclosure is incorporated by reference herein.) Particularly advantageous are dishwasher detergent compositions containing these tensides in amounts of 1–3 wt.%.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The following examples relate to methods for preparing the novel tensides of this invention, as well as to their advantageous properties.

EXAMPLE 1

22.6 g. (0.121 mole) of 1-dodecanol is combined with 1.0 g. of pulverized sodium hydroxide and heated to 160° C. After a clear solution has been formed, 77.4 g. (0.365 mole) of 1,2-epoxytetradecane is added dropwise. The solution is then stirred for 12 hours at this temperature until the epoxide content has dropped below 5%. Within one hour, 106.5 g. (2.420 moles) of ethylene oxide is then introduced in the gaseous form at 170° C.; this quantity of ethylene oxide is absorbed in an exothermic reaction. A pasty, yellowish product results which can optionally be bleached with 1–3% hydrogen peroxide with the addition of a mineral acid. No residual alcohol content can be determined; the polydiol proportion in the product amounts to 4.6%.

It is found in the DOC test that the product is remineralized to an extent of 79.4±4.8%, while a degradability of >90% is determined in the OECD Confirmatory Test.

EXAMPLE 2

67.8 g. (0.366 mole) of 1-dodecanol is reacted in the presence of 1.4 g. of pulverized sodium hydroxide with 232.2 g. (1.094 mole) of 1,2-epoxytetradecane at 200° C. After 2.5 hours the epoxide content of the solution has dropped to 2.6%. The further addition of 372.0 g. (8.454 mole) of ethylene oxide at 180°–200° C. results in a product with 7.2% polydiol content.

| -continued | |
|---|---|
| Tenside according to Example 3 | 3% by weight |
| Sodium carbonate, anhydrous | 20% by weight |
| Pentasodium triphosphate | 50% by weight |
| Sodium metasilicate | 23% by weight |
| Sodium aluminate | 2% by weight |
| Sodium dichloroisocyanurate | 2% by weight |

Table 1 shows the cleansing values obtained with articles used daily in a four-person household, as a comparison between articles cleaned satisfactorily and articles treated in total. The foam level in the machine was determined in each case 20 minutes after starting of the washing cycle and was uniformly 4–5 cm. above the washing liquor.

TABLE 1

Cleansing Effect of Test Detergents and Comparison Detergents

|  | Dishes | Cups | Saucers | Knives | Forks | Spoons | Drinking Glasses |
|---|---|---|---|---|---|---|---|
| Formulation I | 18/18 | 14/16 | 16/16 | 11/13 | 12/14 | 12/12 | 7/7 |
| Formulation II | 18/19 | 16/16 | 14/14 | 10/12 | 14/15 | 8/8 | 8/8 |
| Formulation III | 18/18 | 15/16 | 15/16 | 11/12 | 12/12 | 13/15 | 6/7 |
| Detergent A, Bought | 17/17 | 14/14 | 14/14 | 12/14 | 14/14 | 10/12 | 7/7 |
| Detergent B, Bought | 17/18 | 13/15 | 15/15 | 12/12 | 14/15 | 10/12 | 7/8 |

EXAMPLE 3

72.5 g. (0.25 mole) of a fatty alcohol mixture having an average molar mass of 290 is stirred with 0.9 g. of sodium hydroxide at 220° C. until a clear solution has been formed. At 200° C., the feeding of gaseous ethylene oxide is started; after the ethoxylation has begun, 78.1 g. (0.50 mole) of 1,2-epoxydecane and 330.0 g. (7.50 moles) of ethyl oxide are added in 2 hours simultaneously, but the last 5 ml. of the epoxide are added only after the ethylene oxide feed has been completed. The mixture is then agitated for another hour at 210° C. A residual alcohol value is determined of <0.1% and a polydiol proportion of 1.0% is found. In the DOC degradation test it is found that the product is remineralized to an extent of 56.2±6.1% whereas a degradability of >90% is observed in the OECD Confirmatory Test.

EXAMPLE 4

The products prepared according to Examples 1–3 are combined with the formulations of detergents suitable for automatic dishwashers set forth below and, using the normal dishwashing cycle of a conventional model, compared with two commercially available detergents (amount of detergent employed: 15 g.; operating temperature 60° C.).

| Formulation I: | |
|---|---|
| Tenside according to Example 1 | 3% by weight |
| Pentasodium triphosphate | 50% by weight |
| Sodium metasilicate | 20% by weight |
| Sodium perborate | 25% by weight |
| Sodium aluminate | 2% by weight |
| Formulation II: | |
| Tenside according to Example 2 | 3% by weight |
| Pentasodium triphosphate | 70% by weight |
| Sodium metasilicate | 23% by weight |
| Sodium aluminate | 2% by weight |
| Sodium dichloroisocyanurate | 2% by weight |
| Formulation III: | |

EXAMPLE 5

Table 2 sets forth the values for the surface tension of 2% strength solutions of tensides of this invention as compared to air. All products involve adducts of 1-dodecanol, 1,2-epoxytetradecane, and ethylene oxide, obtained according to the process of Example 1. For comparison purposes, the value of a commercial nonylphenol derivative with propylene (PO) and ethylene (EO) glycol ether groups is also included.

TABLE 2

Surface Tension of a 2% Tenside Solution in Fully Demineralized Water

| No. | Proportion Epoxide | EO | Surface Tension (mN/m.) |
|---|---|---|---|
| 1 | 2 | 19 | 35.5 |
| 2 | 2 | 22 | 36.5 |
| 3 | 2 | 25 | 39.5 |
| 4 | 3 | 18 | 34 |
| 5 | 3 | 25 | 38.5 |
| 6 | 3 | 29 | 37 |
| Comparison | 10 PO | 9 | 34 |

EXAMPLE 6

Table 3 indicates the cloud points of tensides according to the invention as well as the foam levels of 2% solutions in fully demineralized water at 20° C. after 0, 5, and 10 minutes. For this purpose, the sample solution was first shaken ten times in a measuring flask having a capacity of 50 ml. and sealed with a glass stopper, and then the level of the thus-produced foam was measured in dependence on the time. For comparison purposes the measured values of a low-foam nonylphenol-EO-PO adduct are included. The adduct types are denoted by I (block adduct; Example 1) and II (mixed adduct; Example 3).

TABLE 3

Cloud Points and Foam Levels of Tensides of Invention

| No. | Alcohol Component | α-Epoxide/Number | EO | Adduct Type | Cloud Point (*) (°C.) | Foam Levels (cm.) After 0 min. | 5 min. | 10 min. |
|---|---|---|---|---|---|---|---|---|
| 1 | 1-Dodecanol | $C_{14}H_{28}O$/ 2 | 16 | I | 88 | 6.1 | 4.0 | 3.8 |
| 2 | 1-Dodecanol | $C_{14}H_{28}O$/ 2 | 26 | II | 61 | 7.5 | 3.6 | 2.9 |
| 3 | Alcohol Mixture C 10/12 | $C_{14}H_{28}O$/ 2 | 23 | II | 60 | 7.5 | 5.0 | 4.0 |
| 4 | Alcohol Mixture C 10/12 | $C_{14}H_{28}O$/ 3 | 30 | II | 58 | 7.8 | 4.8 | 4.1 |
| 5 | Alcohol Mixture C 10/12 | $C_{10}H_{20}O$/ 2 | 23 | II | 61 | 7.8 | 4.5 | 2.2 |
| 6 | Alcohol Mixture C 10/12 | $C_{10}H_{20}O$/ 3 | 28 | II | 53 | 9.5 | 6.5 | 3.0 |
| 7 | Alcohol Mixture C 16/20 | $C_{10}H_{20}O$/ 2 | 20 | I | cloudy | 6.5 | 2.7 | 2.4 |
| 8 | Alcohol Mixture C 16/20 | $C_{10}H_{20}O$/ 2 | 30 | II | 63 | 7.0 | 2.0 | 1.3 |
| 9 | 1,2-Tetradecanediol | $C_{14}H_{28}O$/ 3 | 34 | II | 53 | 10.0 | 5.0 | 3.2 |
| 10 | 1,4-Butanediol | $C_{14}H_{28}O$/ 4 | 24 | II | 40 | 6.5 | 5.3 | 4.7 |
| Comparison | Nonylphenol | $C_3H_6O$/ 10 | 9 | I | — | 7.0 | 1.2 | 0.6 |

(*) From a 10% solution of the tenside into 25% butyl diglycol/fully demineralized water.

The procding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A biodegradable and low-foaming tenside of the formula (I) or (II)

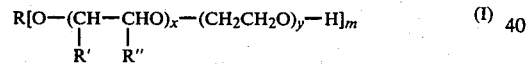

or

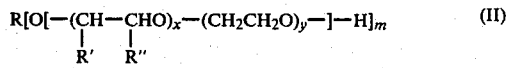

wherein when m is 2,
R is $C_{8-22}$-divalent alkyl, or when m is 1, R is $C_{8-22}$ alkyl or $C_{2-22}$ hydroxyalkyl; and R' and R" each independently is hydrogen or $C_1$-$C_{20}$-alkyl provided that R' and R" are not simultaneously hydrogen, and R' and R" in total have 8–20 carbon atoms;
x is 0.5–5 and y is 5–50;
"---" indicates that the individual x units and the individual y units may be attached to the other x and y units in any order; and
m is 1 or 2 for formula (I) and m is 1 for formula (II).

2. A compound of claim 1 of Formula (I).
3. A compound of claim 1 of Formula (I) wherein x is 2–3 and y is 20–30.
4. A compound of claim 1 of Formula (II).
5. A compound of claim 1 of Formula (II), wherein the sum total of all x is 2–3 and the sum total of all y is 20–30.
6. A compound of claim 1, wherein R is $C_{8-22}$-n-alkyl and m is 1, or R is $C_{8-22}$-n-alkyl and m is 2, the two m units being attached to the 1- and 2-carbon atoms respectively.
7. A compound of claim 1, wherein one of R' and R" is H and the other is $C_{10-14}$ alkyl.
8. A biodegradable and low-foaming tenside of claim 1, wherein 20–80% by weight of the compound is composed of the R—O and x unit portions.
9. A compound of claim 1 wherein m=1.
10. A process for preparing a tenside of claim 1 comprising adding a conventional acidic or alkaline alkoxylation catalyst to a compound $R(OH)_{1-2}$ having active hydrogen; and reacting this reaction mixture at a suitable temperature with an epoxide

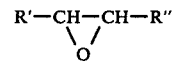

and ethylene oxide.

11. A process of claim 10, whereby a tenside of Formula (I) is prepared, comprising first reacting the mixture of alcohol and catalyst only with the epoxide

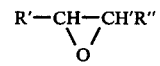

and thereafter reacting the mixture with ethylene oxide.

12. A process of claim 10, whereby a tenside of Formula (II) is prepared, comprising simultaneously reacting the mixture of alcohol and catalyst with the epoxide

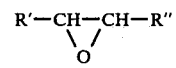

and ethylene oxide.

13. A process of claim 10, wherein the alcohol component is a fatty alcohol of 8–22 carbon atoms or a mixture thereof, or a 1,2-alkanediol of 8–22 carbon atoms or a mixture thereof.

14. A process of claim 10, wherein the epoxide component

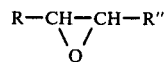

is a 1,2-alkane epoxide of 12–16 carbon atoms or a mixture thereof.

15. A process of claim 10, wherein the reaction is conducted at 150°–230° C. and under normal pressure or excess pressure.

16. A detergent composition comprising a tensile effective amount of a compound of claim 1 and an adjuvant conventional in detergent compositions.

17. The detergent composition of claim 16, which is a dishwasher detergent composition containing said tensides in an amount of 1–3 weight percent.

18. A method of washing articles in a dishwasher using a dishwasher detergent therein, which comprises subjecting the articles to the mechanical washing action of the dishwasher using the dishwasher detergent of claim 17 therein.

* * * * *